(12) United States Patent
Ohigawa et al.

(10) Patent No.: US 7,682,538 B2
(45) Date of Patent: *Mar. 23, 2010

(54) METHOD FOR EXTRUSION MOLDING A MEDICAL APPLICATION TUBE

(75) Inventors: Atsushi Ohigawa, Fukuroi (JP); Kazuhiro Abe, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 72 days.

This patent is subject to a terminal disclaimer.

(21) Appl. No.: 11/961,229

(22) Filed: Dec. 20, 2007

(65) Prior Publication Data

US 2008/0160124 A1    Jul. 3, 2008

(30) Foreign Application Priority Data

Dec. 26, 2006    (JP) .............................. 2006-349617

(51) Int. Cl.
*B29C 47/20* (2006.01)

(52) U.S. Cl. .............. 264/177.1; 264/209.1; 264/209.8; 425/380

(58) Field of Classification Search .............. 264/177.1, 264/209.1, 209.8; 425/380
See application file for complete search history.

(56) References Cited

U.S. PATENT DOCUMENTS

| | | | | |
|---|---|---|---|---|
| 326,865 | A | * | 9/1885 | Hammill .................... 425/380 |
| 353,681 | A | * | 12/1886 | Hurlbut ..................... 425/467 |
| 4,198,367 | A | * | 4/1980 | Burrell ...................... 264/142 |
| 4,398,910 | A | | 8/1983 | Blake et al. |
| 4,465,481 | A | | 8/1984 | Blake |
| 4,919,605 | A | * | 4/1990 | Kousai et al. ................ 425/467 |
| 6,033,204 | A | * | 3/2000 | Iwawaki et al. ......... 425/192 R |

* cited by examiner

*Primary Examiner*—Robert B Davis
*Assistant Examiner*—Joseph Leyson
(74) *Attorney, Agent, or Firm*—Edward S. Jarmolowicz, Esq.; Lawrence A. Chaletsky

(57) ABSTRACT

A method for extrusion molding a medical tube from a soft thermoplastic resin. The method requires the use of a mold that provides flow paths sandwiching the axial portion. The mold comprises a mold body, a pin, and a land portion. The extrusion method involves three processes.

1 Claim, 4 Drawing Sheets

METHOD FOR EXTRUSION MOLDING A MEDICAL APPLICATION TUBE

FIELD OF THE INVENTION

The present invention relates to a mold for extrusion molding a medical application tube employed to drain or supply a medicinal liquid from or to a wound site of a patient and a method for extrusion molding.

BACKGROUND OF THE INVENTION

In conventional practice, a medical application tube has been used to drain the drainage accumulated in the wound site of a patient. There is a medical application tube comprised by a silicone mold including a basal end side portion having a cylindrical shape and a tip end side portion to be indwelled at the wound site of the patient which is formed into a plurality of flow pathways which are sectioned by a central axis therebetween. Further, to this tip end side portion of the medical application tube, slits are formed by notched the outer peripheral side portions of wall portions forming flow pathways along the axial direction, respectively. By providing these slits, the size of the opening of the medical application tube can be increased to effectively suction the drainage (for example Patent Literature 1: Japanese Patent Examined Publication No. H02-17185).

The cross sectional shape of the tip end side portion of this medical application tube (wound site drain catheter) has four flow paths formed by coupling each tip end portion of a cross piece to the ring shaped inner surface and each of four flow paths are communicated with the outside by forming slits by notching the portions each corresponding to between pieces of the ring. Alternatively, three flow paths are formed by coupling each tip end portion of three pieces extended from the center of the ring in three directions to the ring shaped inner surface and each of three flow paths are communicated with the outside by forming slits formed by notching the portions each corresponding to between pieces of the ring.

Further, when the conventional medical application tube as described above is produced, for example, the tube in which the cross sectional shape of the tip end side portion of this medical application tube (wound site drain catheter) has four flow paths formed by coupling each tip end portion of a cross piece to the ring shaped inner surface is formed by extrusion molding and slits are formed by notching formed by processing the portions each corresponding to between pieces of the ring to form the tube for medical tube or it is carried out to directly extrusion molding the medical application tube having slits.

However, in the method for producing the conventional medical application tube, when the slits are formed by processing, there is a problem in that the production cost is increased. While when the medical application tube is once formed into the final shape thereof by extrusion molding and the molding material thereof is soft resin, since, in general, the sliding between this material and the metallic sleeve of the extrusion mold is not good, it is difficult for form the tube by, for example, vacuum sizing. Moreover, even though the material is soft, when it is silicone resin (non thermoplastic resin), the viscosity thereof is high whereby the shape near the shape of mol space of the extrusion mold can easily be molded, while when the molding material comprised by a soft thermoplastic resin such as soft polyurethane or soft polyvinyl chloride is used, the molding by the conventional extrusion molding, same as in the case of silicone resin, can not be carried out.

The invention has been made in the light of these problems and the object of the invention is to provide a mold for an extrusion molding with which a molding a medical application tube having a complex configuration by using a soft thermoplastic resin and an extrusion molding method can be accomplished.

SUMMARY OF THE INVENTION

In order to achieve the above mentioned object, an extrusion mold for the medical application tube in accordance with the invention comprises a soft thermoplastic resin in which a plurality of flow paths made by sandwiching the axial portion are formed therein, in which the mold comprises a mold body having recess portions penetrating from one end to the other end; a pin disposed within said recess portions of said mold body for forming a tapered cylindrical rear side mold space for passing a soft thermoplastic resin molding material between the inner peripheral surfaces of said recess portions; and a land portion for forming a tip end side mold space configuring the tip end portion of said pin and including a cross sectional profile for forming said tube for medical tube between the tip end side portion in the inner peripheral surface of said recess portions, in said cross sectional profiles of the tip end side mold spaces formed by the inner peripheral surfaces of said recess portions and the surface of said land portion, the cross sectional profile at the tip end side portion is same as that of said tube for medical tube and the cross sectional profile at the rear side portion is the intermediate profile of that at the tip end portion of the tip end side mold space and that at the rear end side mold space.

Further, the invention is directed to a method for extruding the medical application tube to mold the medical application tube by using the mold for extrusion molding the medical application tube as set forth above, said method comprises:

a cylinder forming process for forming a molding material into a cylinder by passing the molding material made by a soft thermoplastic resin through the tapered cylindrical rear side mold space provided by placing a pin within the recess of the mold body;

an intermediate profile forming process for forming the cross sectional profile of said molding material formed in said cylinder forming process is configured into the intermediate profile of the ring and the cross sectional profile of the medical application tube at the rear side portion of the tip end side molding space; and a final profile forming process for shaping the cross sectional profile of the molding material formed in said intermediate profile forming process into the cross sectional profile of the medical application tube at the tip end portion of the tip end side molding space.

DESCRIPTION OF FIGURE NOTATIONS 10 represents the medical application tube;
11 represents the outer peripheral portion;
12 represents the partition;
13a, 13b, 13c and 13d each represents the flow path;
14a, 14b and 14c each represents the slit;
20 represents the mold for extrusion molding;
21 represents the mold body;
22 represents the pin;
23 represents the land portion;
24 represents the plate portion;
24a represents the molding slit; and
26a, 27a and 28a each represents the recess.

DETAILED DESCRIPTION OF THE INVENTION

Figure 1:
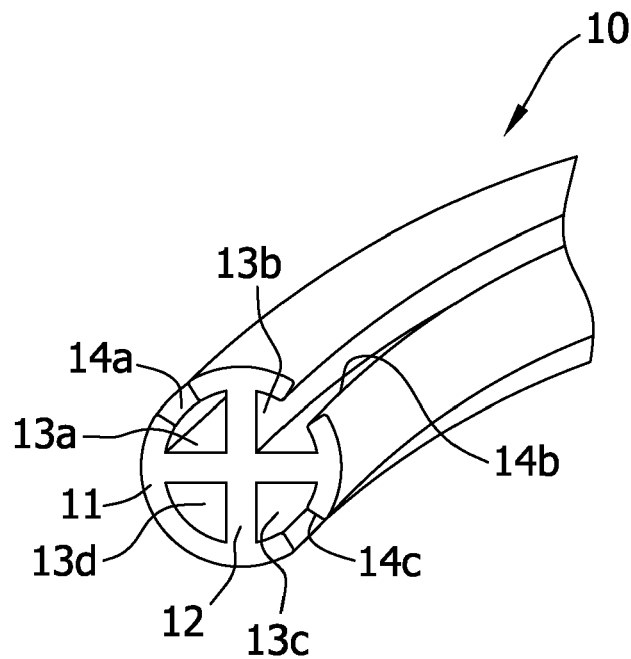
FIG. 1 is a perspective view illustrating the medical application tube formed by the first embodiment in accordance with the invention.

The mold for extrusion molding the medical application tube and the extrusion molding method of the first embodiment in accordance with the invention will now be explained in detail with the reference to the drawings in below. FIG. 1 shows a medical application tube 10 formed by the same embodiment. This medical application tube 10 is comprised by a molded body made by polyurethane having a generally cylindrical outer profile and includes a generally cylindrical outer peripheral portion 11 and a partition portion 12 having a cross shaped cross section formed in the inside of said outer peripheral portion 11 along with the axial direction. The tip end portion of each piece comprising the partition 12 respectively is connected with the inner surface of the outer peripheral portion 11 to divide the inside of the outer peripheral portion 11 into four flow paths 13a, 13b, 13c and 13d. Then, portions corresponding to the flow paths 13a, 13b and 13c of the outer peripheral portion 11 are provided with slits 14a, 14b and 14c parallel to the central axis of the partition 12, respectively, are formed to communicate the flow paths 13a, 13b and 13c with the outside.

Figure 2:
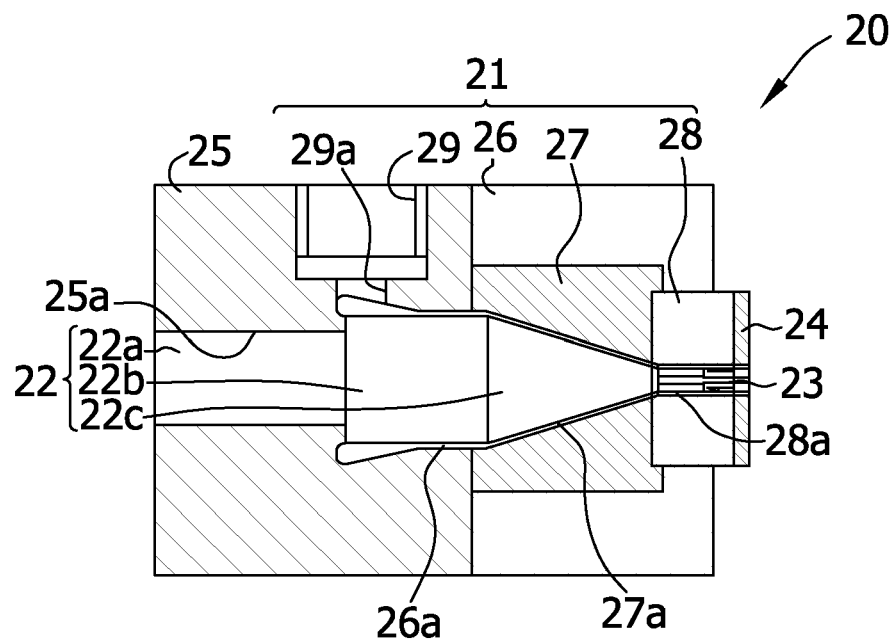
FIG. 2 is a cross sectional view illustrating the mold for extrusion molding.

The medical application tube 10 configured in this way is molded by molding a soft thermoplastic resin of polyurethane with the use of a mold for extrusion molding 20 as shown in FIG. 2. This mold for extrusion molding 20 includes a mold body 21, a pin 22 provided within the mold body 21, a land portion 23 comprising the tip end portion of the pin 22, and a plate portion 24 provided at the tip end portion of the mold body 21. The mold body 21 is comprised by a generally rectangular block body disposed to the rear side (the left side in FIG. 2) including a pin holder portion 25 having a pin holding hole 25a having a circular cross section and penetrating from the center of the rear end surface to the center of the fore end surface, and a bushing holder portion 26 disposed at the fore side of the pin holder portion 25 and provided with a recess 26a for receiving the front side portion of the pin 22.

Then, within the bushing holder portion 26, a bushing 27 is disposed and a bushing 28 is placed in front of the bushing 27. The recess 26a formed in the bushing holder portion 26 is formed into a generally cylindrical space having a slightly larger diameter than that of the pin holding hole 25a. With the upper portion of the rear end side portion of that recess 26a, a material pathway 29 extended from a material inlet 29 formed to the upper surface of the pin holder portion 25 is communicated. Further, in the inside of the bushing holder portion 26, a two stepped bushing mounting recess having a slightly small opening at the front surface is provided at the slightly fore side portion therein, and the bushing is disposed in this recess at the deeper side (rear side) thereof.

From the center of the rear end surface through the center of the fore end surface, a frustoconical recess 27a having a large diameter at the rear side and a small diameter at the fore side is formed. The diameter of the rear end portion of this recess 27a is provided so as to be the same as that of the recess 26a. Then, the bushing 28 having a smaller rectangular shape than that of the bushing 27 is disposed at the front side of the bushing mounting recess of the bushing holder portion 26 such that the fore side of the bushing 28 is projected from the bushing holder portion 26. From the center of the rear end surface through the center of the fore end surface of the bushing 28, a narrow cylindrical recess 28a is formed. The recess 28a is provided so as to have a diameter same as that of the diameter at the fore end portion of the recess 27a. Moreover, the pin holding hole 25a, the recess 26a, the recess 27a and the recess 28a are disposed such that the central axis of each of them is in the same line.

The pin 22 comprises a cylindrical fixed portion 22a fixed within the pin holding hole 25a of the pin holder portion 25; a cylindrical straight portion 22b forwardly extending from the fore end of the fixed portion 22a and having a slightly larger diameter and a shorter length in the axial direction than those of the fixed portion 22a; a frustoconical tapered portion 22c forwardly extending from the fore end of the straight portion 22b and having a gradually decreased diameter at the front end side; and a land portion 23. Then, between the outer peripheral surface of the straight portion 22b and the inner peripheral surface of the recess 26a of the bushing holder portion 26, as well as, between the outer peripheral surface of the tapered portion 22c and the inner peripheral surface of the recess 27a of the bushing 27, gaps through which the molding material is traveled are formed, which comprise the rear side mold space of the present invention.

Figure 3:
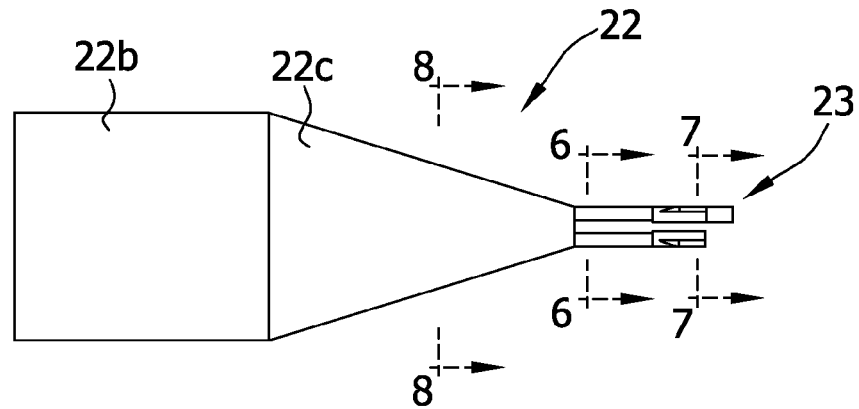
FIG. 3 is a side view illustrating the tip end side portion of the pin.
Figure 4:
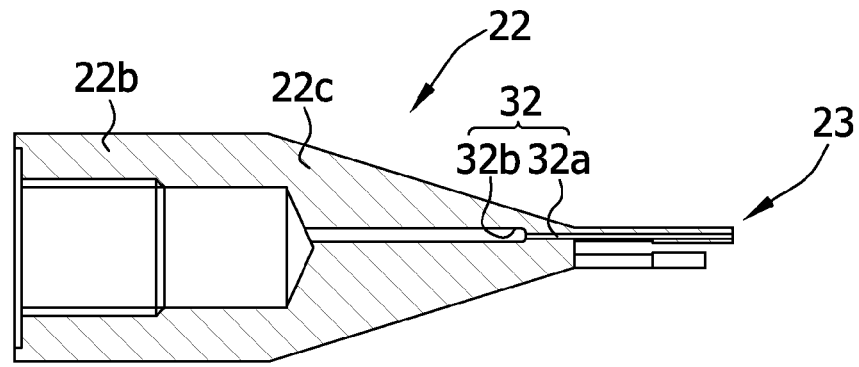
FIG. 4 is a cross sectional view illustrating the tip end side portion of the pin.
Figure 5:
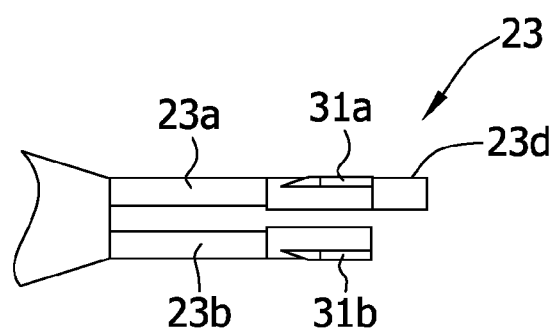
FIG. 5 is an enlarged side view illustrating the land portion.
Figure 6:
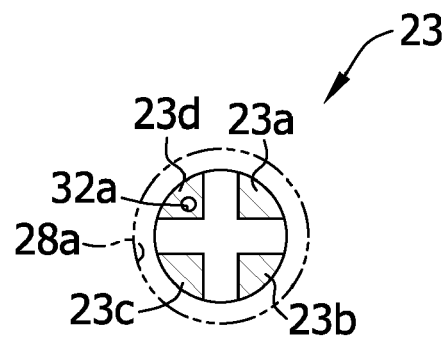
FIG. 6 is a cross section at 6-6 line in FIG. 3.
Figure 7:
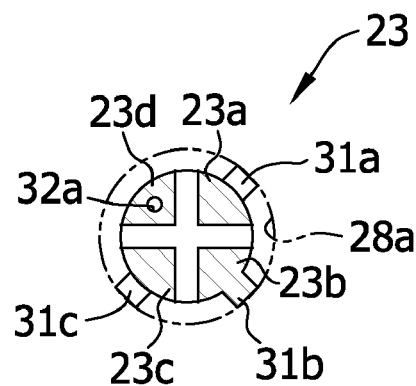
FIG. 7 is a cross section at 7-7 line in FIG. 3.

Further, the land portion 23 configuring the tip end portion of the pin 22 is provided at the tip end portion of the tapered portion 22c as shown in FIGS. 3 and 4 and configured to be four rod like bodies as shown in FIGS. 5 to 7. That is to say, the basal end (rear end side) of the land portion 23, as shown in FIG. 6, is configured to have four rod molded portions 23a, 23b, 23c and 23d each having a sector of cross section. These four rod like molded portions 23a, 23b, 23c and 23d are disposed so as to be parallel in the axial direction such that they together form a generally circular outer periphery portion and provide a cross shaped gap that is the same shape of the partition 12 of the medical application tube 10 therein.

The basal end portion of the land portion 23 is placed to the rear side portion within the recess 28a of the bushing 28 and a cylindrical gap (actually, the thickness of the medical application tube 10 is smaller than that of this gap) having a generally same thickness as that of the outer periphery portion of the medical application tube 10 is provided between the circular portion forming the outer peripheral surface of the basal end portion and the inner peripheral surface of the recess 28a of the land portion 23. Then, this gap forms the rear side portion of the tip end side mold space of the invention. Also, the cross sectional profile of the tip end portion of the land portion 23 is formed to have projections 31a, 31b and 31c provided at each center of arc like portions of the outer peripheral surface of rod like molded portion 23a, 23b and 23c.

The rear end portion of each of projections 31a, 31b and 31c is configured to be an oblique portion such that the portion is increased in the height from the outer peripheral surface of the rod like molded portions 23a, 23b and 23c to forward (in the direction apart from the outer peripheral surface of the rod like molded portions 23, 23b and 23c) with the width gradually increased, and these projections are extended from the tip end portion of the oblique portion to the fore end portion of the rod like molded portion 23a, 23b and 23c with a certain height maintained. To the outer peripheral surface of the rod like molded portion 23d, any projection is provided and the length thereof in the axial direction, as shown in FIG. 5, is longer than those of other rod like molded portions 23a, 23b and 23c.

Figure 8:
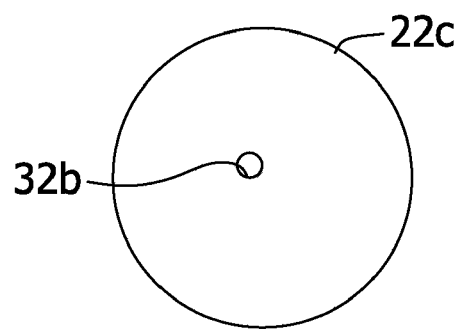
FIG. 8 is a cross section at 8-8 line in FIG. 3.

Then, at the front end surface of the rod like molded portion 23d, the tip end portion of an air outlet 32 extended from the rear side of the pin 22 is opened. The tip end portion 32a of this air outlet 32 is shaped so as to be narrower than the rear side portion 32b and FIG. 8 shows the rear side portion 32b of the air outlet 32 formed within the tapered portion 22c. Further, in the tip end portion of the land portion 23, the portion other than the portion where the tip end of the rod like molded portion 23d is projected is placed to the fore side portion in the recess 28a of the bushing 28 and, between the tip end portion of the land portion 23 and the inner peripheral surface of the recess 28a, a gap having the same shape of the end surface of the medical application tube 10 is formed. That is to say, the tip end surface of each of projections 31a, 31b and 31c is contacted with the inner peripheral surface of the recess 28a, or is provided with a slight gap into which the molding material can not be entered and slits 14a, 14b and 14c are formed to the portions where the projections 31a, 31b and 31c are positioned.

Figure 9:
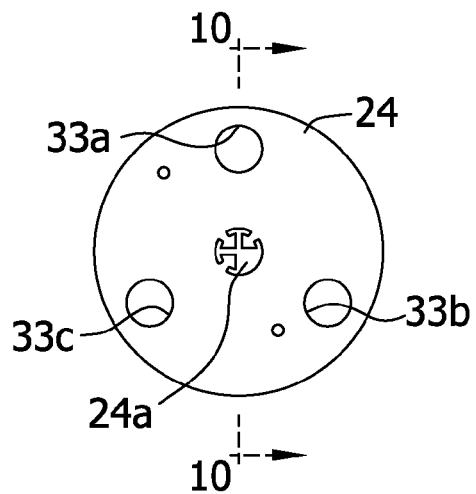
FIG. 9 is a front view of the plate portion.
Figure 10:
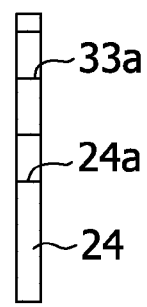
FIG. 10 is a cross section at 10-10 line in FIG. 9.
Figure 11:
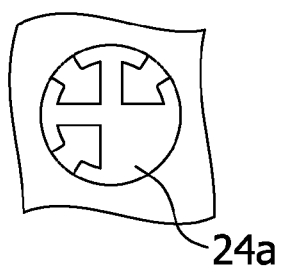
FIG. 11 is an enlarged front view of the molding slits of the plate portion.

The plate portion 24, as shown in FIGS. 9 and 10, is formed into a disc, in which a molding slit 24a penetrating thereof in the thickness direction is formed at the center portion and three bolt insertion holes 33a, 33b and 33c penetrating thereof in the thickness direction are formed to the outer peripheral portion along the circumference thereof with certain intervals. The molding slit 24a, as shown in FIG. 11, is formed into the end surface shape of the medical application tube 10 except for the portion corresponding to the flow path 13d is removed out thereof. Also, the plate portion 24 is fixed to the front surface of the bushing 28 through a bolt (not shown) such that the tip end portion of the rod like molded portion 23d of the land portion 23 is positioned to the corresponding portion of the molding slit 24a to the flow path 13d of the medical application tube 10 (the portion apart from the periphery in the lower right portion in FIG. 11 by a certain distance).

At that time, the center portion of the rear surface of the plate portion 24 is contacted with the tip end surface of the rod like molded portions 23a, 23 and 23c as well as the projections 31a, 31b and 31c, respectively, or is provided with a slight gap into which the molding material can not be entered and slits 14a, 14b and 14c are formed to the portions where the projections 31a, 31b and 31c are positioned. According to this, at the center portion of the plate portion 24, a space having the same shape as that of the end surface of the medical application tube 10 comprised by the molding slit 24a and the rod like molded portion 23d is formed. Then, this space and a gap between the tip end side portion of the land portion 23 described in above and the inner peripheral surface of the recess 28a together form the tip end portion of the tip end side mold space of the invention.

Furthermore, the length of the thickness of the plate portion 24 and the length of the tip end projected portion of the rod like molded portion 23d are same to position the tip end surface of the rod like molded portion 23d on the same surface of the front surface of the plate portion 24. An extrusion molding apparatus, though it is not shown in figures, to which the mold for extrusion molding 20 includes various devices or mechanisms required for extrusion molding by the use of the mold for extrusion molding 20, for example, an adapter for connecting the extrusion molding apparatus to the mold for extrusion molding 20 and delivering the molding material from the material inlet 29 to the material path 29a side; a heating cylinder for heating the molding material to be delivered to the material inlet 29; a screw disposed within the heating cylinder; a control device for controlling various devices provided around the mold for extrusion molding; and the like.

When the medical application tube 10 is molded by using the mold for extrusion molding 20 configured in this way, firstly the mold for extrusion molding 20 is heated to the proper temperature, then, the molding material input to the material inlet (not shown) is delivered by the screw with heating it by the heating cylinder to fill it into the material path 29a through the adapter. Next, the molding material is further delivered to travel the molding material from the material path 29a into the rear side mold space. At that time, the molding material is formed into a cylindrical shape by the gap between the inner peripheral surface of the recess 26a of the bushing holder portion 26 and the outer peripheral surface of the straight portion 22b and further deformed into a cylindrical shape having diameter gradually decreased while passing through the gap between the inner peripheral surface of the recess 27a of the bushing 27 and the outer peripheral surface of the tapered portion 22c.

Then, the molding material is traveled from the gap between the inner peripheral surface of the recess 27a of the bushing 27 and the outer peripheral surface of the tapered portion 22c to the rear side portion of the tip end side mold space formed by the inner peripheral surface of the recess 28a of the bushing 28 and the outer peripheral surface of the basal end portion of the land portion 23. According to this, the cylindrical molding material is deformed into the shape in which the cross shaped partition 12 is configured in the cylinder body. Further, the molding material forwardly travels from the rear end portion of the tip end side mold space to enter the gap between the inner peripheral surface of the recess 28a of the bushing 28 and the tip end side portion of the land portion 23 to provide the profile same as the medical application tube 10.

Then, the molding material is extruded from the molding slit 24a of the plate portion 24 to the outside while maintaining that profile and cooled to provide the medical application tube 10. At this extrusion molding, since the molding material is deformed while heated to the proper temperature and traveled from the material path 29a to the molding slit 24a of the plate portion 24, it can be molded without any difficulty. Further, the obtained medical application tube 10 is a mold having an excellent accuracy in dimension.

As described in above, in the mold for extrusion molding the medical application tube and extrusion molding method thereof in accordance with the embodiment of the invention, the molding material input from the material inlet 29 into the material path 29a is formed into a cylindrical shape and, then, once deformed from the cylindrical shape to the profile having the partition 12 in the cylindrical shape rather than the medical application tube 10. Then, the material is deformed to have the final profile of the medial application tube 10 after it is deformed to have the intermediate profile of that cylindrical shape and the profile of the medical application tube 10.

Accordingly, the configuration of the molding material can be gradually changed whereby the medical application tube 10 having a complex profile can be precisely molded even though the sliding property of the molding material is rather bad relative to each portion of the mold for extrusion molding. Further, since the medical application tube 10 provided with slits 14*a*, 14*b* and 14*c* can be molded in one molding process, the need to provide the slits by process after the molding can be eliminated. As a result, the production processes can be decreased to reduce the production cost.

Moreover, the mold for extrusion molding the medical application tube and extrusion molding method thereof in accordance with the embodiment of the invention is not intended to limit to the embodiments describe din above, various modification thereto can be made within the scope of the invention. For example, in the embodiments described in above, though three slits 14*a*, 14*b* and 14*c* are formed to the medical application tube 10, these slits may be provided to the portion corresponding to the flow path 13*d* in the outer peripheral portion 11 to communicate all flow paths 13*a*, 13*b*, 13*c* and 13*d* with the outside. Further, one or two slits may be formed to the medical application tube 10. Moreover, not only four but also a plurality of flow paths may be provided to the medical application tube. Also, the profile of the medical application tube is not limited to the profile of the embodiments described in above may be suitably changed. Further, the soft thermoplastic resin comprising the medical application tube is not limited to polyurethane and other material such as polyvinyl chloride may be employed.

In the mold for extrusion molding the tube for medical tube in accordance with the invention configured in that way described in above, the cross sectional profile at the rear side portion in the cross sectional profiles of the tip end side spaces formed by the inner peripheral surface of the tip end side portion of the recess portions of the mold body and the surface of the land portion configuring the tip end portion of the pin is configured into the intermediate of the cross sectional profile of the medical application tube that is the cross sectional profile at the tip end portion of the tip end side mold space and a ring shape that is the cross sectional profile at the tip end portion of the rear side mold space. Therefore, the molding material is once deformed from the ring shaped cross sectional profile into the intermediate profile near the cross sectional profile of the medical application tube and, then, the intermediate profile can be deformed to the cross sectional profile that is the final profile rather than deforming from the ring shaped cross sectional profile at the rear side mold space formed between the recess portions of the mold body into the cross sectional profile of the tube for medical tube directly.

According to this, the change quantity of the shape by one deformation can be decreased whereby the tube for medical tube having a complex shape can be precisely molded even though the slidability is little or largely bad relative to the mold for the molding material. The medical application tube extruded from the mold for extrusion molding will be slightly extended at the outside of the mold for extrusion molding. Therefore, the size of the cross sectional profile at the tip end portion of the tip end side mold space which is the same as the cross sectional profile of the medical application tube of the invention will be slightly larger than that of the cross sectional profile of the medical application tube.

The another configurational characteristic of the extrusion mold for the medical application tube in accordance with the invention is that a plate part including a recess for forming the outer surface that forms a surface along the outside of the molding material traveled from the rear side mold space is disposed at the tip end side of said recess portions of the mold body, one portion of said land portion is extended to the predetermined position within the recess portion forming the outer surface of said plate part, thereby forming a flow path occluded at the peripheral surface by the medical application tube to be molded in the position where said land portion is located within the plate part, as well as, a space formed by the recess portion forming the outer surface of said plate part and the portion where the land portion is located within the plate part being the tip end portion of the rear side mold space.

In this mold for extrusion molding the medical application tube, a plate part including a recess for forming the outer surface that forms a surface along the outside of the medical application tube is disposed at the tip end side of said recess portions of the mold body, and one portion of a land portion is extended into the outer surface forming recess of this plate part (forward in the axial direction). Therefore, it can be configured that the predetermined flow path in the plurality of flow paths included by the medical application tube is occluded at the peripheral surface other than both ends thereof. One portion of the land part extending into the outer surface forming recess of the plate part in this case may be of several numbers thereof.

According to this, a plurality of flow paths occluded at their peripheral surfaces can be formed to the medical application tube. When the flow path provided with the slit formed to the predetermined portion of the medical application tube is communicated with the outside, the predetermined portion of the land portion is protruded toward the outer peripheral direction to contact with the predetermined portion of the outer surface forming recess of the plate part, or a slight gap into which the molding material can not be entered is formed between that portion and the inner peripheral surface of the outer surface forming recess, thereby forming the slit at that portion. Therefore, the slit is formed to every flow path, the need to provide the plate part can be eliminated.

Yet another configurational characteristic of the extrusion mold for the medical application tube in accordance with the invention is that a cross sectional profile of the rear side portion of the tip end side mold space is formed such that each tip end portion of the cross piece is coupled to the ring like inner surface to form four flow pathways, the cross sectional profile of the tip end portion of the tip end side mold space is formed such that the predetermined portion of the ring like portion is notched to communicate at least one of four flow pathways with the outside. According to this, since an abnormal shaped tube to which slits are provided can be molded by extrusion molding in one time, the need to provide slits by processing after the molding can be eliminated. As a result, the production processes can be reduced to attempt to decrease the manufacturing cost. In this case, the slits formed by notched the ring like portion may be provided with one flow path or 2 to 4 of a plurality of flow path.

Further, the configurational characteristic of the extrusion molding method for molding the medical application tube in accordance with the invention is that the method is the extrusion molding method for molding the medical application tube that molds the medical application tube using the extrusion mold described in above, in which the method comprises a cylinder forming process for forming a molding material into a cylinder by passing the molding material made by a soft thermoplastic resin through the tapered cylindrical rear side mold space provided by placing a pin within the recess of the mold body; an intermediate profile forming process for forming the cross sectional profile of said molding material formed in said cylinder forming process is configured into the intermediate profile of the ring and the cross sectional profile of the medical application tube at the rear side portion of the tip end side molding space; and a final profile forming process for shaping the cross sectional profile of the molding material formed in said intermediate profile forming process into the cross sectional profile of the medical application tube at the tip end portion of the tip end side molding space.

The extrusion molding method for the medical application tube comprised by this way includes the cylinder forming process for forming the molding material into the cylindrical shape; the intermediate profile forming process for forming the cross sectional profile of the cylindrical molding material into the intermediate profile of the ring and the cross sectional profile of the medical tube; and the final profile forming process for shaping the cross sectional profile of the molding material formed in said intermediate profile forming process into the cross sectional profile of the medical application tube. Accordingly, the cross sectional profile of the molding material is deformed from the ring like cross sectional profile of the rear side mold space formed between the recess portion of the mold body and the pin to the intermediate profile near the cross sectional profile of the medical application tube once, then, further deformed to the final profile of the cross sectional profile of the medical application tube from that intermediate profile. Therefore, the change quantity in profile by one deformation of the molding material can be decreased whereby the medical application tube having a complex profile can be precisely molded even though the sliding the material relative to the mold.

Further, the configurational characteristic of the extrusion molding method of the medical application tube in accordance with the invention is that the cross sectional profile of the molding material formed in the intermediate profile forming process is formed into the configuration in which four flow paths are formed by connecting each tip end portion of the cross piece to the ring like inner surface, and the cross sectional profile of the molding material forming in the final profile forming process is configured to the shape in which at least one flow path of four flow paths is communicated with the outside by notching the predetermined portion of the ring like portion. According to this, since an abnormal shaped tube to which slits are provided can be molded by extrusion molding in one time, the need to provide slits by processing after the molding can be eliminated. Further, the production processes can be reduced to attempt to decrease the manufacturing cost.

What is claimed is:

1. A method for extruding a medical tube using a mold for extrusion molding,
wherein the mold comprises an extrusion mold for a medical tube made from a soft thermoplastic resin in which a plurality of flow paths are formed therein by sandwiching the axial portion, wherein the mold further comprises a mold body having recess portions penetrating from one end to the other end;

a pin disposed within said recess portions of said mold body for forming a tapered cylindrical rear space for passing a soft thermoplastic resin molding material between the inner peripheral surfaces of said recess portions; and a land portion for forming a tip end space configuring the tip end portion of said pin and including a cross sectional shape for forming said medical tube between the rip end portion in the inner peripheral surface of said recess portions, in said cross sectional shapes of the tip end spaces formed by the inner peripheral surfaces of said recess portions and the surface of said land portion, the cross sectional shape at the tip end portion is the same as that of said medical tube and the cross sectional shape at the rear portion is the intermediate shape of that at the tip end portion of the tip end space and that at the rear end space, wherein, in the extrusion mold, a cross sectional shape of the rear portion of the tip end space is formed such that each tip end portion of a cross piece is coupled to a ring like inner surface to form four flow pathways, the cross sectional shape of the tip end portion of the tip end space is formed such that the predetermined portion of the ring like portion is notched to communicate at least one of the four flow pathways with the outside, wherein said method for extruding comprises:

a first process for forming a material of a soft thermoplastic resin into a cylinder by passing the material through the tapered cylindrical rear space;

a second process for forming the cross sectional shape of said material formed in said first process into an intermediate shape between a ring and a cross sectional shape of the medical tube at the rear portion of the tip end space; and a third process for shaping the cross sectional shape of the material formed in said second process into the cross sectional shape of the medical tube at the tip end portion of the tip end space.

* * * * *